United States Patent
Jun et al.

(10) Patent No.: US 7,289,661 B2
(45) Date of Patent: Oct. 30, 2007

(54) APPARATUS AND METHOD FOR INSPECTING A SUBSTRATE

(75) Inventors: Chung-Sam Jun, Suwon-si (KR); Sun-Yong Choi, Seongnam-si (KR); Kwang-Soo Kim, Yongin-si (KR); Joo-Woo Kim, Seoul (KR); Jeong-Hyun Choi, Yongin-si (KR); Dong-Jin Park, Gyeonggi-do (KR)

(73) Assignee: Samsung Electronics Co., Ltd., Suwon, Kyungki-do (KR)

( * ) Notice: Subject to any disclaimer, the term of this patent is extended or adjusted under 35 U.S.C. 154(b) by 828 days.

(21) Appl. No.: 10/661,633

(22) Filed: Sep. 15, 2003

(65) Prior Publication Data

US 2004/0086171 A1 May 6, 2004

(30) Foreign Application Priority Data

Oct. 30, 2002 (KR) .................... 10-2002-0066613

(51) Int. Cl.
*G06K 9/00* (2006.01)
(52) U.S. Cl. .................................... 382/149
(58) Field of Classification Search ........ 382/141–149, 382/199; 348/86, 92; 702/33, 35, 127
See application file for complete search history.

(56) References Cited

U.S. PATENT DOCUMENTS 5,917,588 A 6/1999 Addiego
6,215,551 B1 4/2001 Nikoonahad et al.
6,829,047 B2 12/2004 Fujii et al.
6,829,559 B2* 12/2004 Bultman et al. ............ 702/155
2003/0030050 A1* 2/2003 Choi ............................. 257/4

FOREIGN PATENT DOCUMENTS

| JP | 2000-207562 | 7/2000 |
| JP | 2002-310929 | 10/2002 |
| KR | 10-2001-0044250 | 6/2001 |

* cited by examiner

*Primary Examiner*—Daniel Mariam
(74) *Attorney, Agent, or Firm*—Lee & Morse, P.C.

(57) ABSTRACT

An automated and integrated substrate inspecting apparatus for performing an EBR/EEW inspection, a defect inspection of patterns and reticle error inspection of a substrate includes a first stage for supporting a substrate; a first image acquisition unit for acquiring a first image of a peripheral portion of the substrate supported by the first stage; a second stage for supporting the substrate; a second image acquisition unit for acquiring a second image of the substrate supported by the second stage; a transfer robot for transferring the substrate between the first stage and the second stage; and a data processing unit, connected to the first image acquisition unit and the second image acquisition unit, for inspecting results of an edge bead removal process and an edge exposure process performed on the substrate using the first image, and for inspecting for defects of patterns formed on the substrate using the second image.

22 Claims, 6 Drawing Sheets

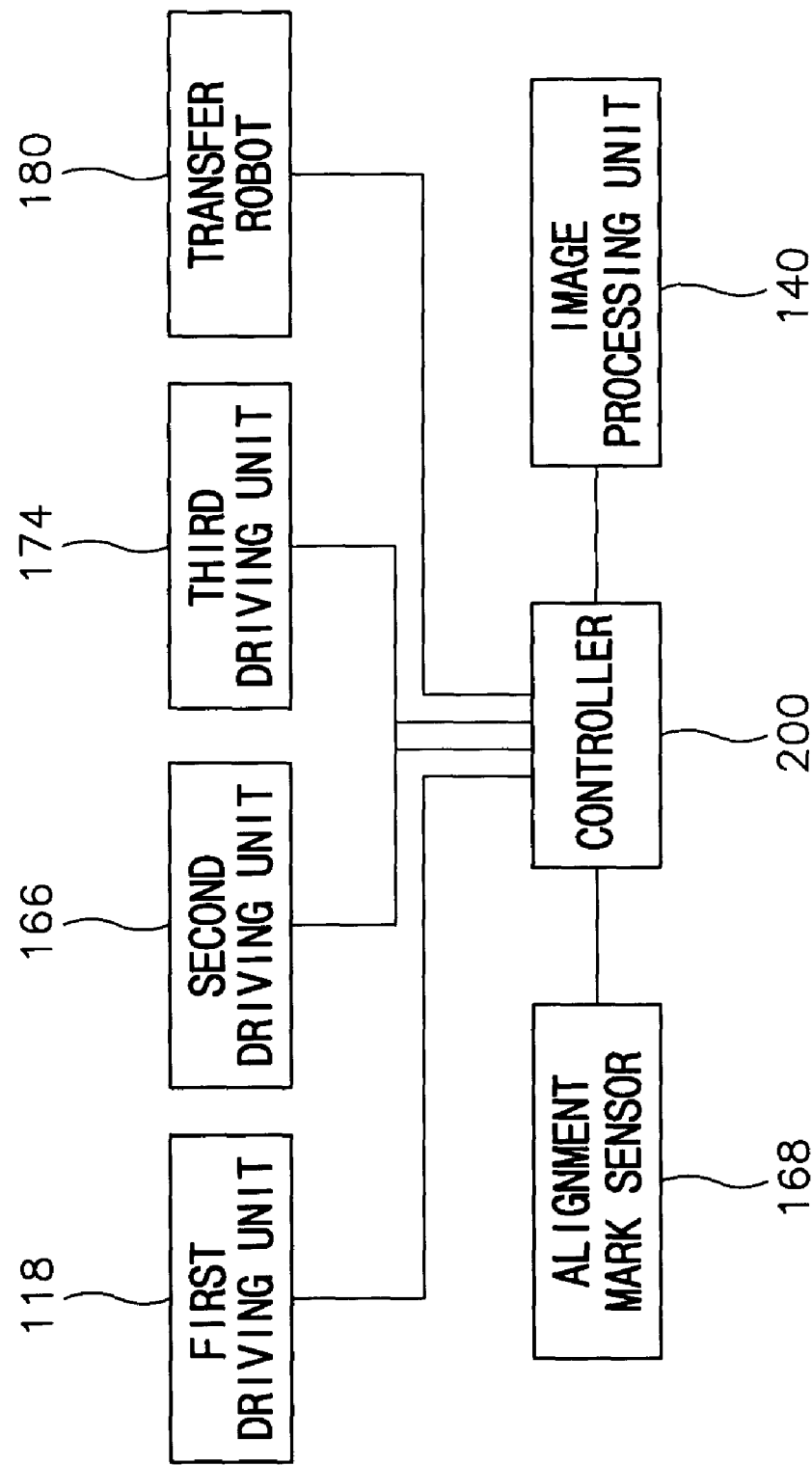

APPARATUS AND METHOD FOR INSPECTING A SUBSTRATE

BACKGROUND OF THE INVENTION

1. Field of the Invention

The present invention relates to an apparatus and a method for inspecting a substrate. More particularly, the present invention relates to an apparatus and a method for inspecting defects in photoresist patterns formed on a semiconductor substrate and inspecting results of an edge bead removal (EBR) process and an edge exposure of wafer (EEW) process in a manufacturing process of a semiconductor device.

2. Description of the Related Art

Generally, semiconductor devices are manufactured through a three-step process. First, a fabricating process is performed for forming an electrical device, such as a transistor and a capacitor, on a silicon wafer used as a semiconductor substrate. Second, an inspecting process is performed for inspecting electrical characteristics of semiconductor devices formed on the semiconductor substrate. Third, a packaging process is performed for packaging the semiconductor devices to protect the semiconductor devices and for enabling the installation of the semiconductor devices in the various information communication devices.

During the manufacturing process, various films are formed on the semiconductor substrate by a film deposition process. Subsequently, the films are formed into the patterns having electrical characteristics using a photolithography process and an etching process. The photolithography process is performed for forming a photoresist film and for forming the photoresist film into photoresist patterns. The photoresist patterns are used as an etching mask in the etching process. The photolithography process has been noticed in semiconductor manufacturing technology as the patterns formed on the semiconductor substrate become minute and the aspect ratio of the pattern more increases.

A microscope inspecting process is performed for inspecting the photoresist patterns formed using the photolithography process before the etching process is performed. The microscope is used for inspecting defects of the photoresist patterns and for inspecting results of the performance of the EBR process for removing a photoresist film from a peripheral portion of the semiconductor substrate and the EEW process concerning the peripheral portion of the semiconductor substrate. It is not possible to objectively and statistically manage a microscope inspecting process because the microscope inspecting process depends significantly on a level of skill of an operator. In addition, the microscope inspecting process is not able to cope effectively with increases in a size of the semiconductor substrate. In addition, the time required to perform the microscope process may increase due to the performance of various other inspecting processes.

Several conventional systems and devices have been developed in an attempt to solve the foregoing problems. The conventional systems and device, however, are not able to perform the various inspecting processes because the conventional systems and devices used for performing the inspecting process address only specific portions of the substrate or patterns.

SUMMARY OF THE INVENTION

In an effort to overcome at least some of the above-mentioned problems, one exemplary embodiment of the present invention provides an automated and integrated apparatus for performing the entirety of an EBR/EEW inspecting process, a reticle error inspecting process and a photoresist pattern inspecting process with respect to a substrate. In addition, another exemplary embodiment of the present invention provides a method for inspecting defects of patterns formed on a substrate through an EBR/EEW inspecting process, a reticle error inspecting process and a photoresist pattern inspecting process with respect to a substrate.

The apparatus for inspecting the substrate includes a first stage for supporting a substrate; a first image acquisition unit for acquiring a first image of a peripheral portion of the substrate supported by the first stage; a second stage for supporting the substrate; a second image acquisition unit for acquiring a second image of the substrate supported by the second stage; a transfer robot for transferring the substrate between the first stage and the second stage; and a data processing unit, connected to the first image acquisition unit and the second image acquisition unit, for inspecting results of an edge bead removal process and an edge exposure process performed on the substrate using the first image, and for inspecting for defects of patterns formed on the substrate using the second image.

Preferably, the first image acquisition unit includes a charge coupled device camera positioned over the substrate supported by the first stage for acquiring the first image; and a light source for illuminating the peripheral portion of the substrate.

The data processing unit may calculate a distance from a side surface of the substrate to a side surface of a photoresist film including the patterns in the first image and inspects results of an edge bead removal process and an edge exposure process performed on the substrate from the calculated distance.

The apparatus may further include a first driving unit and a second driving unit for causing a relative motion between the substrate supported by the first stage and the charge coupled device camera so that the first image acquisition unit acquires the first image. The first driving unit and the second driving unit may include a first driving unit for moving the charge coupled device camera along a flat zone portion of the substrate supported by the first stage; and a second driving unit for rotating the first stage.

Preferably, the second image acquisition unit includes an illuminating section for directing an illuminating light at an angle towards the substrate supported by the second stage; and a detecting section for detecting light reflected from the substrate to acquire the second image. The second image may include a reticle identification number or a reticle identification pattern for identifying a reticle used for forming the patterns.

The illuminating section of the second image acquisition unit may include a beam generator for providing a laser beam, a beam expander for expanding the laser beam, a reflecting mirror for reflecting the expanded laser beam, a beam deflector for deflecting the reflected laser beam, and a focusing lens for focusing the deflecting laser beam onto the substrate supported by the second stage.

The apparatus may further include a third driving unit for moving the second stage so that the focused laser beam scans the entire surface of the substrate supported by the second stage.

The data processing unit may detect defects of the patterns formed on the substrate by comparing the second image with a reference image.

The apparatus may further include a data storage unit for storing the reference image or for storing inspection results processed by the data processing unit.

The apparatus may further include an alignment mark sensor positioned above the substrate supported by the first stage for aligning the substrate supported by the first stage.

The apparatus may further include a display unit for displaying the inspection results or for displaying the first and second images.

According to an embodiment of the present invention, a method for inspecting a substrate includes loading a substrate on a first stage, acquiring a first image of a peripheral portion of the substrate loaded on the first stage, inspecting results of an edge bead removal process and an edge exposure of wafer process performed on the substrate using the first image, transferring the substrate onto a second stage, acquiring a second image of another portion of the substrate supported by the second stage, and inspecting defects of patterns formed on the substrate using the second image.

Preferably, the substrate includes a silicon wafer and acquiring the first image further includes rotating the substrate and continuously acquiring the first image of the peripheral portion of the rotating substrate using an image acquisition unit disposed over the peripheral portion of the substrate.

Preferably, inspecting the results of the edge bead removal process and the edge exposure of wafer process further includes calculating a distance from a side surface of the substrate to a side surface of a photoresist film using the first image, and judging the results of the edge bead removal process and the edge exposure of wafer process using the calculated distance.

Preferably, acquiring the second image further includes illuminating a light onto the substrate supported by the second stage, moving the substrate so that the light scans an entire surface of the substrate supported by the second stage, and acquiring the second image a light reflected from the substrate.

According to an embodiment of the present invention, the various inspecting processes are performed using a single inspecting apparatus so that the efficiency of the various inspecting processes may be improved and the required time of the various inspecting processes may be reduced. In addition, technical inspection data of the various inspecting processes may be effectively managed, and the various inspecting processes may be objectively and statistically managed so that the reliability of the various inspecting processes can be improved.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIG. 6 illustrates a block diagram of a controller.

DETAILED DESCRIPTION OF THE INVENTION

Korean Patent Application No. 2002-66613, filed on Oct. 30, 2002, and entitled: "Apparatus for Inspecting a Substrate," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
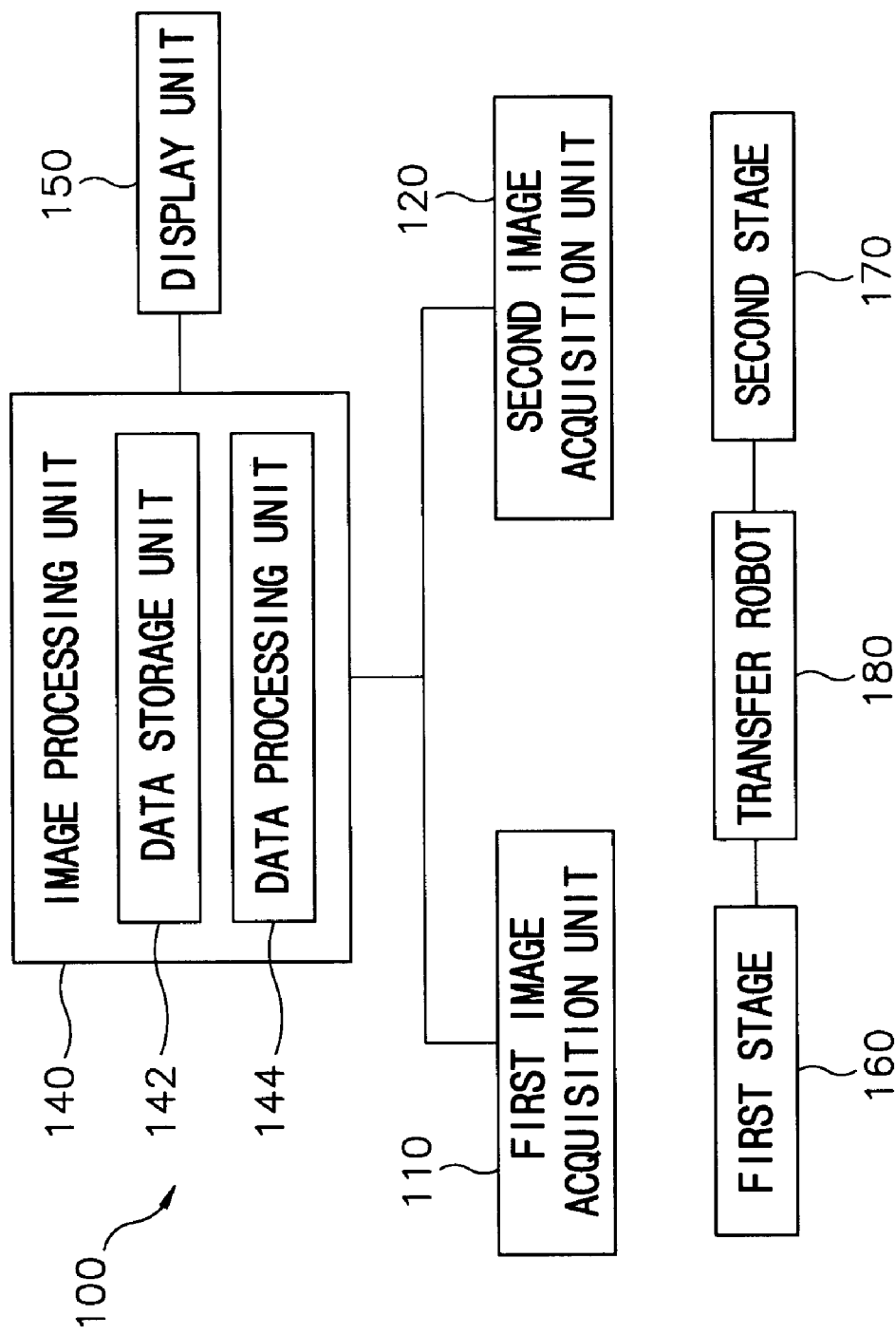
FIG. 1 is a block diagram illustrating an apparatus for inspecting a substrate according to an exemplary embodiment of the present invention.

FIG. 1 is a block diagram illustrating an apparatus for inspecting a substrate according to an exemplary embodiment of the present invention.

Referring to FIG. 1, a substrate inspecting apparatus 100 includes a first image acquisition unit 110, a second image acquisition unit 120 and an image processing unit 140.

During a manufacturing process, a photoresist film having a photoresist pattern is formed on a semiconductor substrate. The first image acquisition unit 110 acquires a first image corresponding to a peripheral portion of the semiconductor substrate having the photoresist film. The second image acquisition unit 120 acquires a second image corresponding to a remaining central portion of the semiconductor substrate not included in the first image, i.e., not the peripheral region. The image processing unit 140 performs an EBR/EEW inspection, a photoresist pattern inspection and a reticle error inspection using first image data and second image data.

The image processing unit 140 includes a data storage unit 142 and a data processing unit 144. The data storage unit 142 may include a conventional memory device and a conventional hard disk. The data processing unit 144 may include a conventional microprocessor.

In operation, the data processing unit 144 calculates a distance from a side surface of the semiconductor substrate to a side surface of the photoresist film in the first image and inspects the results of the performance of the EBR/EEW processes from the calculated distance.

The data storage unit 142 stores a reference image corresponding to a semiconductor substrate subjected to a normal photolithography process. The data processing unit 144 performs the photoresist pattern inspection and the reticle error inspection by comparing the second image with the reference image.

The data storage unit 142 stores and manages the first image data acquired by the first image acquisition unit 110, the second image data acquired by the second image acquisition unit 120 and the inspection results processed by the data processing unit 144.

In addition, a display unit 150 is connected to the image processing unit 140 and displays the inspection results, the first image and the second image.

The substrate inspecting apparatus further includes a first stage 160, a second stage 170 and a transfer robot 180. The first image acquisition unit 110 acquires the first image from the semiconductor substrate while the substrate is supported by the first stage 160. The second image acquisition unit 120 acquires the second image from the semiconductor substrate while the substrate is supported by the second stage 170. The transfer robot 180 transfers the semiconductor substrate from a cassette for receiving a plurality of semiconductor substrates onto the first stage 160, transfers the semiconductor substrate having been subjected to the EBR/EEW inspecting process from the first stage 160 onto the second stage 170, and returns the semiconductor substrate having been subjected to the photoresist patterns and reticle error inspecting processes from the second stage 170 into the cassette.

Accordingly, the EBR/EEW inspecting process, the photoresist patterns inspecting process and the reticle error inspecting process can be automated. Further, the substrate inspecting apparatus can be effectively employed in a manufacturing process of a semiconductor substrate having a diameter of about 300 mm in accordance with a trend toward the automation of 300 mm semiconductor substrate manufacturing apparatuses.

Figure 2:
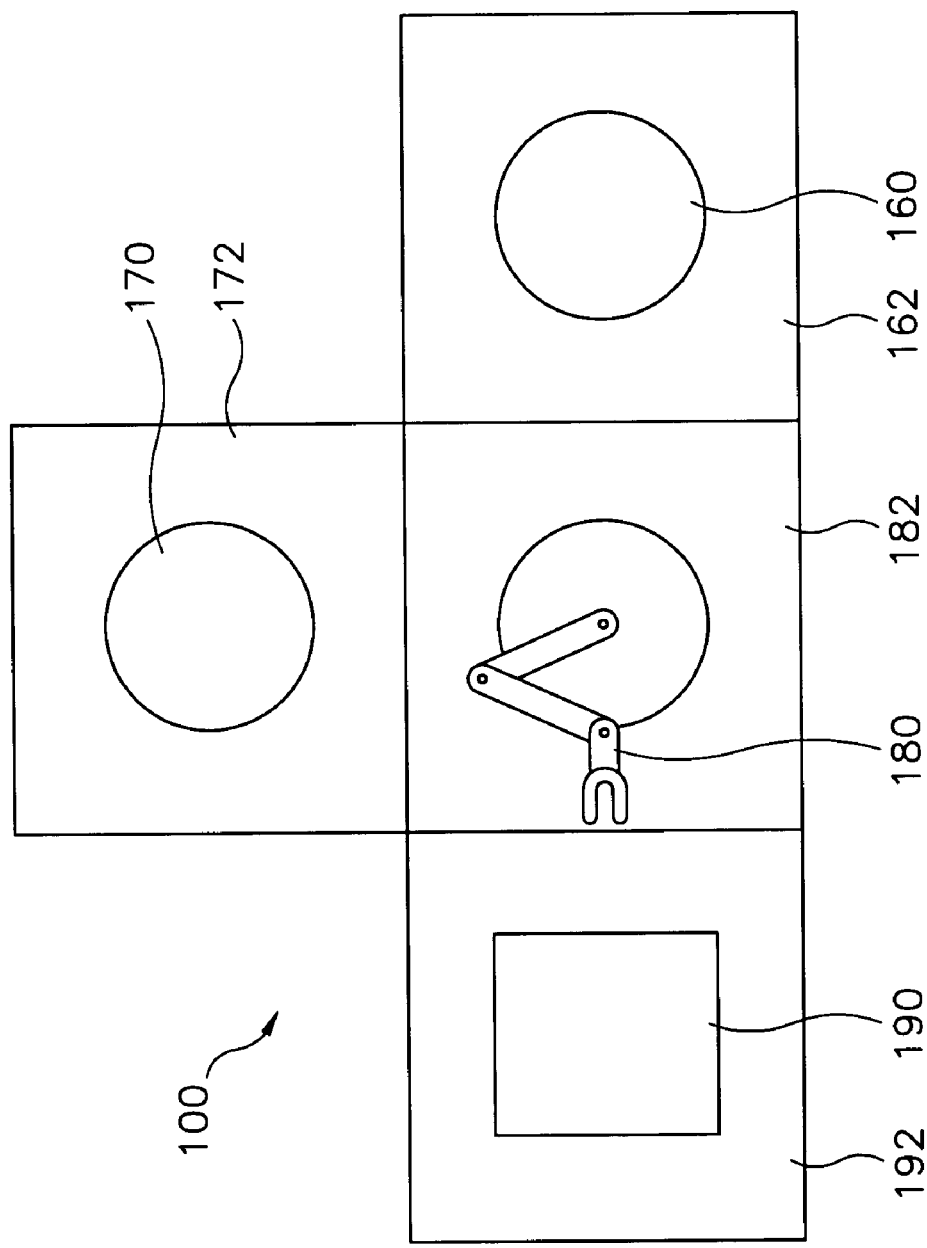
FIG. 2 illustrates a schematic view of the apparatus for inspecting a substrate as shown in FIG. 1.

FIG. 2 illustrates a schematic view of the apparatus for inspecting a substrate as shown in FIG. 1.

Referring to FIG. 2, the substrate inspecting apparatus 100 includes a first inspecting chamber 162 including the first stage 160, a second inspecting chamber 172 including the second stage 170, a transfer chamber 182 including the transfer robot 180 and a storage chamber 192 including the cassette 190 for receiving the plurality of semiconductor substrates.

The first inspecting chamber 162, the second inspecting chamber 172 and the storage chamber 192 are each connected to a sidewall of the transfer chamber 182. In operation, the transfer robot 180 transfers a semiconductor substrate to be inspected from the cassette 190 in the storage chamber 192 onto the first stage 160 of the first inspecting chamber 162. The transfer robot 180 then transfers the semiconductor substrate having been subjected to the EBR/EEW inspecting process from the first stage 160 of the first inspecting chamber 162 onto the second stage 170 of the second inspecting chamber 172. Next, the transfer robot 180 returns the semiconductor substrate having been subjected to the photoresist patterns and reticle error inspecting processes from the second stage 170 of the second inspecting chamber 172 into the cassette 190 of the storage chamber 192.

The photoresist film including the photoresist patterns is formed on the semiconductor substrate using a photolithography process. The photoresist patterns are used as an etching mask during the etching process in order to form patterns having electrical characteristics. The patterns may include a contact hole, a via hole, a recess, or the like for forming electrical devices and metal wiring.

The photoresist film is formed by coating a surface of the semiconductor substrate with a photoresist composition and baking the photoresist composition. At this time, a bead is formed at the peripheral portion and the side surface of the semiconductor substrate. The bead is easy to crumble during the photolithography and the etching processes and acts as a particle source during subsequent processes. Accordingly, the photoresist film formed at the peripheral portion and the side surface of the semiconductor substrate is removed through the EBR and the EEW processes.

The EBR process is performed to remove the photoresist film formed at the peripheral portion and the side surface of the semiconductor substrate using a solvent. The EEW process is a performed to expose the peripheral portion of the semiconductor substrate to ultraviolet rays and to develop the peripheral portion exposed to the ultraviolet rays. When the EBR/EEW processes are not properly performed, the photoresist film remaining at the peripheral portion and the side surface of the semiconductor substrate acts as a particle source in subsequent processes. Therefore, the results of the performance of the EBR/EEW processes require inspection.

Figure 3:
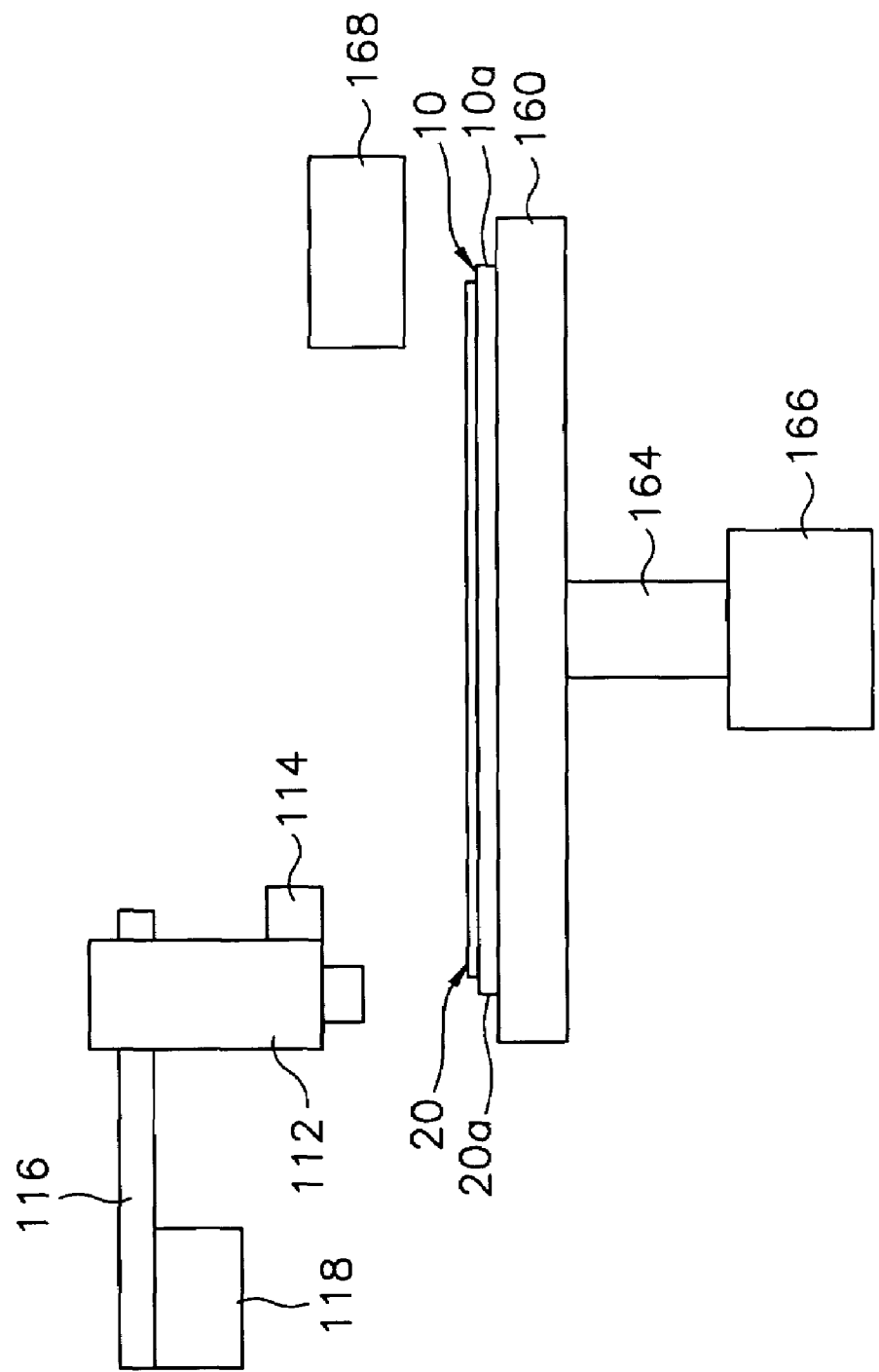
FIG. 3 illustrates a schematic side view of a first image acquisition unit.
Figure 4:
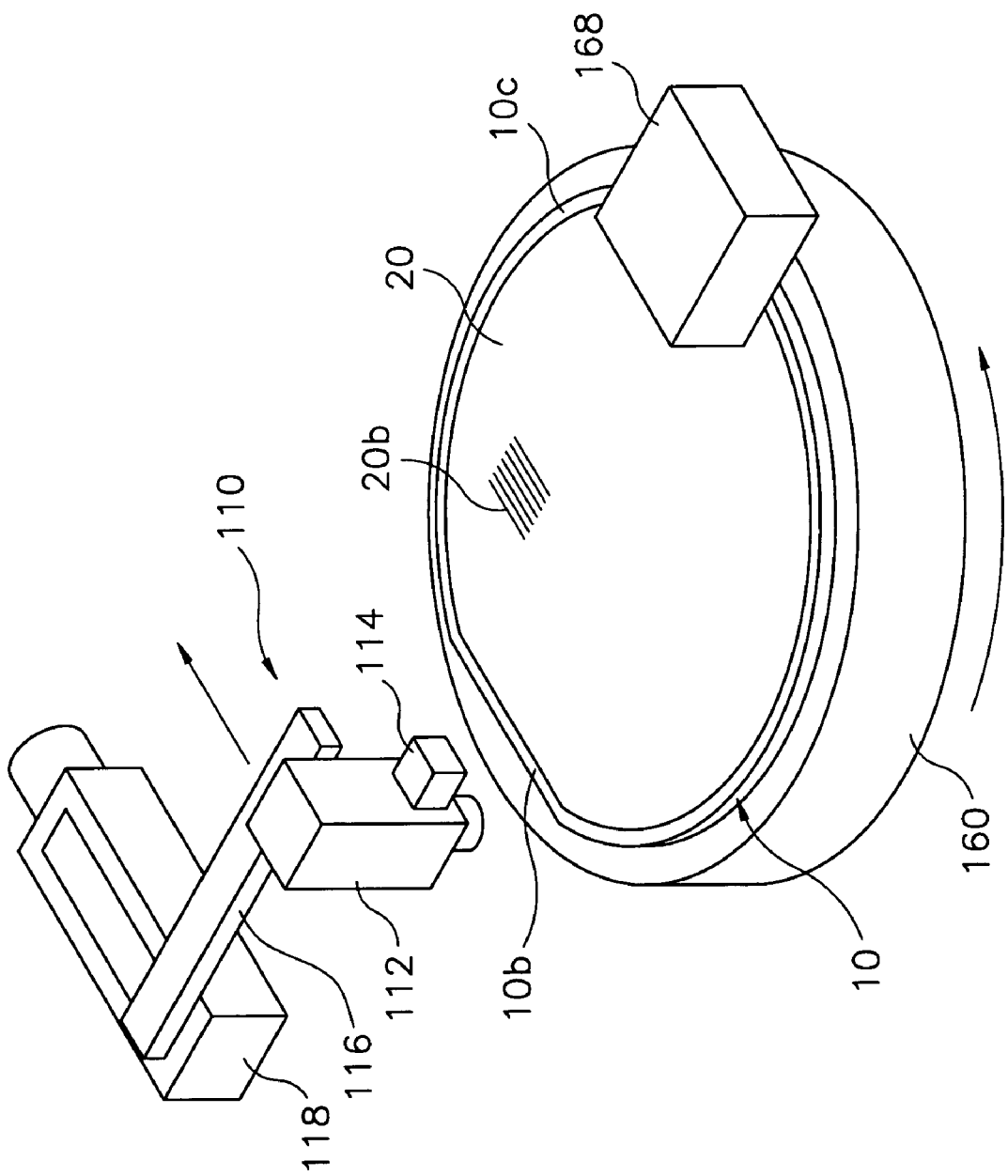
FIG. 4 illustrates an elevated, perspective view of the first image acquisition unit as shown in FIG. 3.

FIG. 3 illustrates a schematic side view of a first image acquisition unit 110. FIG. 4 illustrates an elevated, perspective view of the first image acquisition unit 110 as shown in FIG. 3.

Referring to FIGS. 3 and 4, a semiconductor substrate 10 having a flat zone portion 10b and circular portion 10c is transferred onto the first stage 160 by the transfer robot (180 of FIG. 2). Though not illustrated in the figures, the semiconductor substrate 10 is loaded using a loading member, such as lift pins. The first image acquisition unit 110 is positioned over the semiconductor substrate 10 supported by the first stage 160 in order to acquire the first image corresponding to the peripheral portion of the semiconductor substrate 10.

The first image acquisition unit 110 includes a charge coupled device (CCD) camera 112 and a light source 114 for illuminating the peripheral portion of the semiconductor substrate 10. The first image acquisition unit 110 is connected to a first driving unit 118 for moving the first image acquisition unit 110 through a horizontal arm 116. The first stage 160 is connected to a second driving unit 166 for rotating the first stage 160 through a rotating shaft 164. The light source 114 may include a light emitting diode (LED).

The first driving unit 118 may include a motor and a power transmission device of a ball screw type. In addition, the first driving 118 can include various straight-line driving devices.

The rotating shaft 164 connects a lower portion of the first stage 160 with the second driving unit 166. A step motor capable of controlling a rotating angle may be used as the second driving unit 166.

An alignment mark sensor 168 is disposed over the semiconductor substrate 10 supported by the first stage 160 in order to align the semiconductor substrate 10. The alignment mark sensor 168 is positioned opposite to (i.e., across from) the first acquisition unit 110 and senses an alignment mark formed on the semiconductor substrate 10 in order to align the semiconductor substrate 10.

The first driving unit 118, the second driving unit 166 and the alignment mark sensor 168 are connected to a controller (200 of FIG. 6), and the controller aligns the semiconductor substrate 10 by operating the second driving unit 166 according to a sensing signal from the alignment mark sensor 168. In addition, the controller operates the first driving unit 118 and the second driving unit 166 sequentially so that the first image acquisition unit 110 is able to successively acquire the first image.

In operation, the first image acquisition unit 110 moved by the first driving unit 118 acquires an image of a flat zone portion of the semiconductor substrate 10, and then acquires an image of a circular portion of the semiconductor substrate 10 rotated by the second driving unit 166. The acquired first image is transmitted to the image processing unit (140 of FIG. 1), and the image processing unit 140 inspects the results of the performance of the EBR/EEW processes with respect to the semiconductor substrate 10 according to gray levels of the acquired first image.

In the acquired first image, the gray levels corresponding to a first boundary portion between the first stage 160 and the semiconductor substrate 10 and a second boundary portion between the semiconductor 10 and photoresist film 20 having photoresist patterns 20b are higher than those of the other portions. That is, the gray levels of first pixels corresponding to a side surface 10a of the semiconductor substrate 10 and second pixels corresponding to a side surface 20a of the photoresist film 20 are higher than those of the other portions. The image processing unit 140 calculates the distance between the first pixels and the second pixels having relatively high gray levels, and inspects the results of performing the EBR/EEW processes by comparing the calculated distance with a predetermined distance. When a difference between the calculated distance and the predetermined distance is greater than an allowable limit, the results of the EBR/EEW processes are determined to be defective.

The data storage unit (142 of FIG. 1) stores the predetermined distance. The data processing unit (144 of FIG. 1) performs the EBR/EEW inspection by comparing the calculated distance with a predetermined distance. The data storage unit 142 stores and manages the results of the EBR/EEW inspection, and the stored results of the EBR/EEW inspection may be applied with research data or analysis data.

Similarly, an EBR/EEW inspection of a notch-type semiconductor substrate may be also performed in a similar manner as described above.

Subsequently, the transfer robot 180 transfers the semiconductor substrate 10 having been subjected to the EBR/EEW inspecting process from the first stage 160 of the first inspecting chamber 162 onto the second stage 170 of the second inspecting chamber 172.

Figure 5:
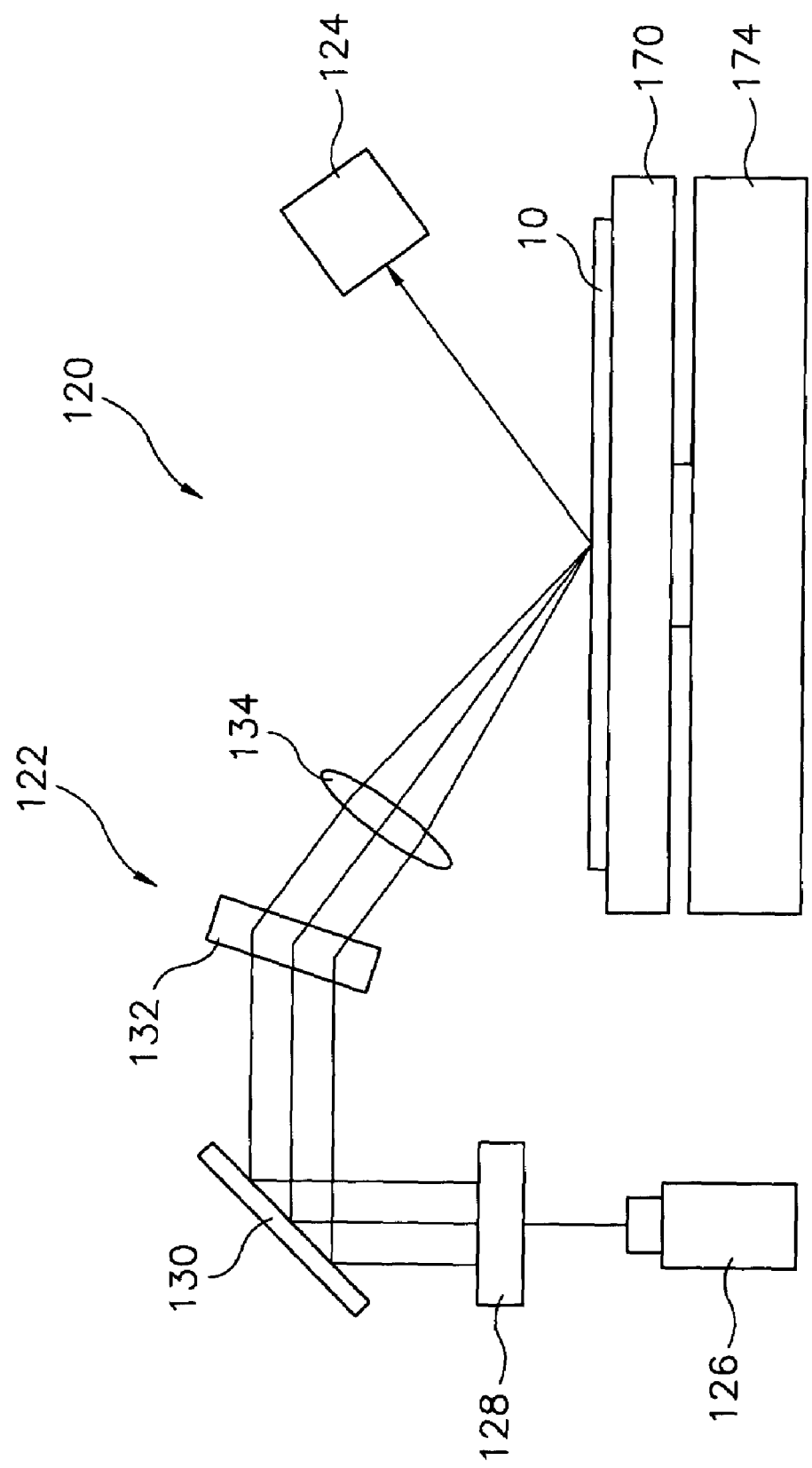
FIG. 5 illustrates a schematic side view of a second image acquisition unit.

FIG. 5 illustrates a schematic side view of a second image acquisition unit.

Referring to FIG. 5, the second image acquisition unit 120 includes an illuminating section 122 for directing an illuminating light at a grazing angle toward the semiconductor substrate 10 supported by the second stage 170, and a detecting section 124 for detecting the light reflected from the semiconductor substrate 10 in order to acquire the second image.

The illuminating light includes a laser beam. A beam generator 126 provides the laser beam, and a beam expander 128 expands the laser beam provided from the beam generator 126. A reflecting mirror 130 then changes the direction of the expanded laser beam, a beam deflector 132 deflects the expanded laser beam, and a focusing lens 134 focuses the deflected laser beam onto the semiconductor substrate 10 at a grazing angle while the semiconductor substrate 10 is supported by the second stage 170. The beam deflector 132 and the focusing lens 134 adjust the grazing angle and spot size of the laser beam, respectively.

Subsequently, the laser beam illuminated onto the semiconductor substrate 10 is reflected by the semiconductor substrate 10. The detecting section 124 detects the reflected light from the semiconductor substrate 10, thereby acquiring the second image.

The second image acquisition unit 120 may further include various elements, such as a filtering member for passing a laser beam having a specific wavelength, a member for uniformly forming the laser beam, a collimator for parallelizing the laser beam, a member for changing a passage of the laser beam, or the like.

As described above, the substrate inspecting apparatus acquires the second image from the reflected light from the semiconductor substrate. However, various alternate image acquisition devices may be employed in the substrate inspecting apparatus.

Additionally, a third driving unit 174 for moving the second stage 170 is connected to a lower portion of the second stage 170 so that the focused laser beam scans the entire surface of the semiconductor substrate 10 supported by the second stage 170. The third driving unit 174 two-dimensionally moves the second stage 170 in an x-axis and a y-axis direction according to a control signal of the controller (not shown).

A defect inspection of the semiconductor substrate 10 includes a defect inspection of the photoresist patterns (20b of FIG. 4), a particle inspection and a reticle error inspection. The defect inspection of the photoresist patterns 20b is performed to inspect for defects of the photoresist patterns 20b, such as an irregularity of a critical dimension, a falling, or a scratch in the photoresist patterns. The particle inspection is performed for inspecting for particles remaining on the semiconductor substrate 10. The reticle error inspection is performed for identifying whether the reticle is normally used in the photolithography process.

When the defect inspection of the photoresist patterns 20b and the particle inspection are performed, the second image includes the entire surface of the semiconductor substrate. When the reticle error inspection is performed, the second image includes a specific area of the surface of semiconductor substrate 10. The specific area for reticle error inspection includes a reticle identification number or a reticle identification pattern for identifying a reticle used for forming the photoresist patterns. Alternately, the reticle inspection may be performed with the second image including the entire surface of the semiconductor substrate 10.

The data storage unit (142 of FIG. 1) stores a first reference image corresponding to properly formed photoresist patterns and a second reference image corresponding to a reticle identification number or a reticle identification pattern of the semiconductor substrate subjected to a normal photolithography process. The data processing unit (144 of FIG. 1) inspects the defects of the semiconductor substrate 10 by comparing the acquired second image with the first reference image and the second reference image. The data storage unit 142 stores and manages the results of the defect inspection of the semiconductor substrate, and the results of the defect inspection may be applied with research data or analysis data.

Additionally, the second image acquisition unit 120 and the image processing unit 140 may be used for inspecting the various patterns to be formed on the semiconductor substrate 10 as well as the photoresist film 20 including the photoresist patterns 20b.

FIG. 6 is a block diagram illustrating a controller.

Referring to FIG. 6, the alignment mark sensor 168 is connected to the controller 200. The controller 200 aligns the semiconductor substrate 10 supported by the first stage 160 (see FIG. 3) by operating the second driving unit 166 according to the sensing signal from the alignment mark sensor 168.

The controller 200 operates the first driving unit 118 and the second driving unit 166 sequentially so that the first image acquisition unit 110 successively acquires the first image of the semiconductor substrate 10 supported by the first stage 160. When the EBR/EEW inspection of the flat zone portion (10b of FIG. 4) of the semiconductor substrate 10 is terminated, the image processing unit 140 transmits a first ending signal to the controller 200. The controller 200 stops the operation of the first driving unit 118 according to the first ending signal, and then operates the second driving unit 166. When the EBR/EEW inspection of the circular portion (10c of FIG. 4) is finally stopped, the image processing unit 140 transmits a second ending signal to the controller 200. The controller 200 stops the operation of the second driving unit 166 according to the second ending signal.

The controller 200 operates the transfer robot 180 in order to transfer the semiconductor substrate 10 having been subjected to the EBR/EEW inspecting process from the first stage 160 onto the second stage 170.

The controller 200 then operates the third driving unit 174 so that the second image acquisition unit 120 acquires the second image of the semiconductor substrate 10 supported the second stage 170. The image processing unit 140 transmits a processing result signal to the controller 200 in real time. The controller 200 adjusts a moving direction and speed of the second stage 170 by controlling an operation of the third driving unit 174 according to the processing result signal.

When the defect inspection of the semiconductor substrate 10 is terminated, the controller 200 operates the transfer robot 180 in order to return the semiconductor substrate 10 having been subjected to the defect inspecting process from the second stage 170 into the cassette 190.

According to an embodiment of the present invention, an automated and integrated substrate inspecting apparatus is able to successively perform the EBR/EEW inspecting process, the defect inspection process of the patterns and the reticle error inspecting process. At this time, the substrate inspecting apparatus may selectively perform any one of the inspecting processes. Additionally, efficiency and reliability of the inspecting processes may be improved, and the time required for the inspecting processes may be reduced.

In addition, the automation of the various inspecting processes is able to basically eliminate operational errors and subjective defect judgment of an operator. The continuous management of the inspection results enables the objective and statistical evaluation of the performance of the various inspecting processes. In addition, the inspection results may be applied with research data or analysis data.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for inspecting a substrate, comprising:
   a first stage for supporting a substrate;
   a first image acquisition unit for acquiring a first image of a peripheral portion of the substrate supported by the first stage;
   a second stage for supporting the substrate;
   a second image acquisition unit for acquiring a second image of the substrate supported by the second stage;
   a transfer robot for transferring the substrate between the first stage and the second stage; and
   a data processing unit, connected to the first image acquisition unit and the second image acquisition unit, for inspecting results of an edge bead removal process and an edge exposure process performed on the substrate using the first image, and for inspecting for defects of patterns formed on the substrate using the second image.

2. The apparatus for inspecting a substrate as claimed in claim 1, wherein the first image acquisition unit comprises:
   a charge coupled device camera positioned over the substrate supported by the first stage for acquiring the first image; and
   a light source for illuminating the peripheral portion of the substrate.

3. The apparatus for inspecting a substrate as claimed in claim 2, wherein the light source is a light emitting diode.

4. The apparatus for inspecting a substrate as claimed in claim 2, wherein the data processing unit calculates a distance from a side surface of the substrate to a side surface of a photoresist film including the patterns in the first image and inspects results of an edge bead removal process and an edge exposure process performed on the substrate from the calculated distance.

5. The apparatus for inspecting a substrate as claimed in claim 2, further comprising a first driving unit and a second driving unit for causing a relative motion between the substrate supported by the first stage and the charge coupled device camera so that the first image acquisition unit acquires the first image.

6. The apparatus for inspecting a substrate as claimed in claim 5, wherein the first driving unit and the second driving unit comprise:
   a first driving unit for moving the charge coupled device camera along a flat zone portion of the substrate supported by the first stage; and
   a second driving unit for rotating the first stage.

7. The apparatus for inspecting a substrate as claimed in claim 1, wherein the second image acquisition unit comprises:
   an illuminating section for directing an illuminating light at an angle towards the substrate supported by the second stage; and
   a detecting section for detecting light reflected from the substrate to acquire the second image.

8. The apparatus for inspecting a substrate as claimed in claim 7, wherein the illuminating section comprises:
   a beam generator for providing a laser beam;
   a beam expander for expanding the laser beam;
   a reflecting mirror for reflecting the expanded laser beam;
   a beam deflector for deflecting the reflected laser beam; and
   a focusing lens for focusing the deflecting laser beam onto the substrate supported by the second stage.

9. The apparatus for inspecting a substrate as claimed in claim 8, further comprising a third driving unit for moving the second stage so that the focused laser beam scans the entire surface of the substrate supported by the second stage.

10. The apparatus for inspecting a substrate as claimed in claim 7, wherein the second image comprises a reticle identification number or a reticle identification pattern for identifying a reticle used for forming the patterns.

11. The apparatus for inspecting a substrate as claimed in claim 1, wherein the data processing unit detects defects of the patterns formed on the substrate by comparing the second image with a reference image.

12. The apparatus for inspecting a substrate as claimed in claim 11, further comprising a data storage unit for storing the reference image.

13. The apparatus for inspecting a substrate as claimed in claim 1, further comprising an alignment mark sensor positioned above the substrate supported by the first stage for aligning the substrate supported by the first stage.

14. The apparatus for inspecting a substrate as claimed in claim 1, further comprising a data storage unit for storing inspection results processed by the data processing unit.

15. The apparatus for inspecting a substrate as claimed in claim 14, further comprising a display unit for displaying the inspection results.

16. The apparatus for inspecting a substrate as claimed in claim 1, further comprising a display unit for displaying the first and the second images.

17. The apparatus for inspecting a substrate as claimed in claim 1, wherein the first stage is in a first inspection chamber, and the second stage is in a second inspection chamber.

18. A method for inspecting a substrate, comprising:
   loading a substrate on a first stage;
   acquiring a first image of a peripheral portion of the substrate loaded on the first stage;

inspecting results of an edge bead removal process and an edge exposure of wafer process performed on the substrate using the first image;

transferring the substrate onto a second stage;

acquiring a second image of another portion of the substrate supported by the second stage; and inspecting defects of patterns formed on the substrate using the second image.

19. The method for inspecting a substrate as claimed in claim 18, wherein the substrate includes a silicon wafer, and acquiring the first image further comprises rotating the substrate and continuously acquiring the first image of the peripheral portion of the rotating substrate using an image acquisition unit disposed over the peripheral portion of the substrate.

20. The method for inspecting a substrate as claimed in claim 18, wherein inspecting the results of the edge bead removal process and the edge exposure of wafer process further comprises:

calculating a distance from a side surface of the substrate to a side surface of a photoresist film using the first image; and judging the results of the edge bead removal process and the edge exposure of wafer process using the calculated distance.

21. The method for inspecting a substrate as claimed in claim 18, wherein acquiring the second image further comprises:

illuminating a light onto the substrate supported by the second stage;

moving the substrate so that the light scans an entire surface of the substrate supported by the second stage; and acquiring the second image a light reflected from the substrate.

22. The method for inspecting a substrate as claimed in claim 18, wherein the first stage is in a first inspection chamber, and the second stage is in a second inspection chamber.

* * * * *